United States Patent
Werkheiser

(10) Patent No.: US 11,191,686 B2
(45) Date of Patent: Dec. 7, 2021

(54) PNEUMATIC CHAIR JACK

(71) Applicant: D.T. Davis Enterprises, Ltd., Allentown, PA (US)

(72) Inventor: Jason K. Werkheiser, Fogelsville, PA (US)

(73) Assignee: D.T. Davis Enterprises, Ltd., Allentown, PA (US)

( * ) Notice: Subject to any disclaimer, the term of this patent is extended or adjusted under 35 U.S.C. 154(b) by 0 days.

(21) Appl. No.: 16/321,169

(22) PCT Filed: Apr. 10, 2018

(86) PCT No.: PCT/US2018/026832
§ 371 (c)(1),
(2) Date: Jan. 28, 2019

(87) PCT Pub. No.: WO2018/191228
PCT Pub. Date: Oct. 18, 2018

(65) Prior Publication Data
US 2020/0022859 A1    Jan. 23, 2020

Related U.S. Application Data

(60) Provisional application No. 62/484,927, filed on Apr. 13, 2017.

(51) Int. Cl.
*A61G 7/10* (2006.01)
*A61G 5/14* (2006.01)
*A61G 7/02* (2006.01)

(52) U.S. Cl.
CPC .................................. *A61G 7/02* (2013.01); *A61G 5/14* (2013.01)

(58) Field of Classification Search
CPC ...... A61G 7/1021; A61G 5/14; A61G 7/1019; A61G 7/1265; A61G 7/1013; A61G 7/10;
(Continued)

(56) References Cited

U.S. PATENT DOCUMENTS 5,561,873 A    10/1996  Weedling
5,669,086 A *   9/1997  Garman ................... B65G 7/04
                                                      5/86.1
(Continued)

FOREIGN PATENT DOCUMENTS

GB    2358797 A  *  8/2001  ........... A61G 7/1003
GB    2529954 A     3/2016

OTHER PUBLICATIONS

International Search Report and Written Opinion for corresponding International patent application No. PCT/US2018/026832, dated Aug. 2, 2018.
(Continued)

*Primary Examiner* — Peter M. Cuomo
*Assistant Examiner* — Alison N Labarge
(74) *Attorney, Agent, or Firm* — Duane Morris LLP

(57) ABSTRACT

A multi-cell inflatable jack includes a plurality of jack elements. Each of the plurality of jack elements includes a body having a predetermined perimeter shape and defining a perimeter chamber and a central chamber. A valve is coupled to the body and configured to provide air flow to one of the perimeter chamber or the central chamber. A plurality of flow control stringers are located between the first chamber portion and the second chamber portion and are configured to control an air flow rate into each of the perimeter chamber and the central chamber. At least one fastener is formed on the body and configured to attach the jack element to at least one additional jack element in a multi-cell stack.

16 Claims, 11 Drawing Sheets

(58) Field of Classification Search
CPC .... A61B 6/0485; A47G 9/1027; A47C 27/087
See application file for complete search history.

(56) References Cited

U.S. PATENT DOCUMENTS

| | | | | |
|---|---|---|---|---|
| 6,015,471 | A * | 1/2000 | Rimington | A61G 5/14 156/274.4 |
| 6,073,291 | A | 6/2000 | Davis | |
| 2003/0159212 | A1 * | 8/2003 | Patrick | A61G 7/103 5/81.1 R |
| 2005/0132490 | A1 * | 6/2005 | Davis | A61G 7/1021 5/81.1 R |
| 2005/0283905 | A1 | 12/2005 | Johnson | |
| 2006/0218728 | A1 * | 10/2006 | Liu | A47C 27/10 5/710 |
| 2007/0000048 | A1 * | 1/2007 | Davis | A61G 7/1021 5/81.1 R |
| 2014/0230154 | A1 * | 8/2014 | Palumbo | A47C 27/081 5/706 |
| 2014/0232156 | A1 * | 8/2014 | Mills | A61G 7/1057 297/338 |
| 2018/0289182 | A1 * | 10/2018 | McEntee | A47G 9/1081 |

OTHER PUBLICATIONS

European Patent Office, Extended European Search Report, dated Nov. 5, 2020.

* cited by examiner

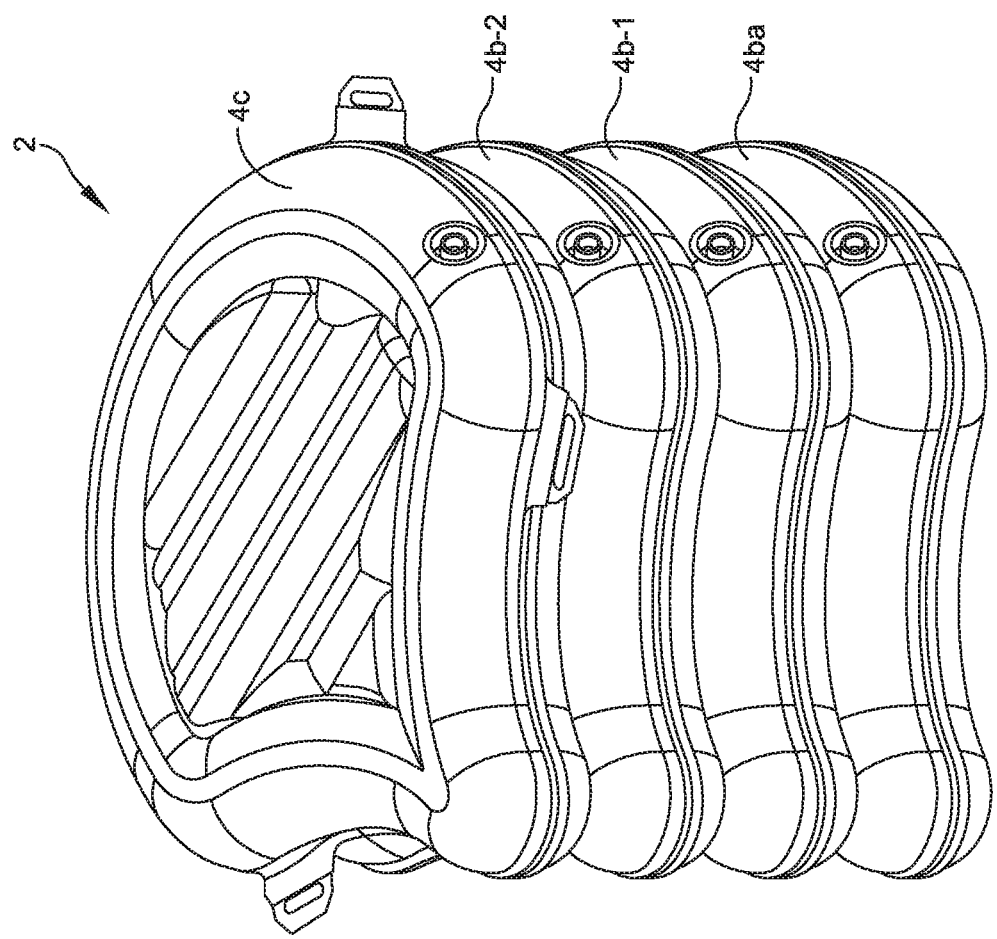

PNEUMATIC CHAIR JACK

CROSS-REFERENCE TO RELATED APPLICATIONS

This application is a National Stage Application, filed under 35 U.S.C. 371, of International Patent Application No. PCT/US2018/026832, filed on Apr. 10, 2018, which claims benefit to U.S. Provisional Patent Appl. Ser. No. 62/484,927, filed on Apr. 13, 2017, and entitled "PNEUMATIC CHAIR JACK," contents of both of which are incorporated herein by reference in their entireties.

BACKGROUND

Raising a patient from a seated position to a standing position presents risks for both the patient and the caregiver(s) assisting the patient. A patient positioned on a lower surface, such as a floor, ground, low-table, etc., may be unstable when attempting to stand (or transition to kneeling, etc.), may experience forces on joints (e.g., shoulder joints) that can be injured by a caregiver lifting the patient, and/or may attempt to place weight (or other forces) on injured extremities prior to realizing an injury exists. Caregivers may also suffer injuries when attempting to assist a patient in standing, such as back injuries, falling injuries (do to unstable patients falling), etc.

Current systems for raising a patient from seated position include direct caregiver intervention which, as discussed above, presents injury risks for both caregivers and the patient. Other solutions require lifting devices, such as arm straps, that require larger lifting machines and that exert forces on other joints of a patient during a lifting procedure.

SUMMARY

In various embodiments, a jack element is disclosed. The jack element includes a body having a predetermined perimeter shape and defining a perimeter chamber and a central chamber. A valve is coupled to the body and configured to provide air flow to one of the perimeter chamber or the central chamber. A plurality of flow control stringers located between the first chamber portion and the second chamber portion. The plurality of flow control stringers are configured to control an air flow rate into each of the perimeter chamber and the central chamber. At least one fastener is formed on the body and is configured to attach the jack element to at least one additional jack element in a multi-cell stack.

In various embodiments, a system is disclosed. The system includes a first jack element and a second jack element. Each of the first and second jack elements include a body including a predetermined perimeter shape and defining a perimeter chamber and a central chamber. A valve is coupled to the body and configured to provide air flow to one of the perimeter chamber or the central chamber. A plurality of flow control stringers are located between the first chamber portion and the second chamber portion. The plurality of flow control stringers are configured to control an air flow rate into each of the perimeter chamber and the central chamber. At least one fastener is formed on the body. The first jack element is configured to be attached to the second jack element by the at least one fastener on each of the first jack element and the second jack element.

In various embodiments, a method is disclosed. The method includes a step of positioning a multi-cell inflatable jack under a patient. The multi-cell inflatable jack comprises a plurality of inflatable jack elements. A first of the plurality of inflatable jack elements is inflated to raise a patient from a seated position to a first height. A second of the plurality of inflatable jack elements is inflated to raise a patient from the first height to a second height. The second height is configured to position the patient in a standing position.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein:

FIG. 1A illustrates a pneumatic chair jack including a plurality of single cell jack elements, in accordance with some embodiments.

DETAILED DESCRIPTION

Figure 1C:
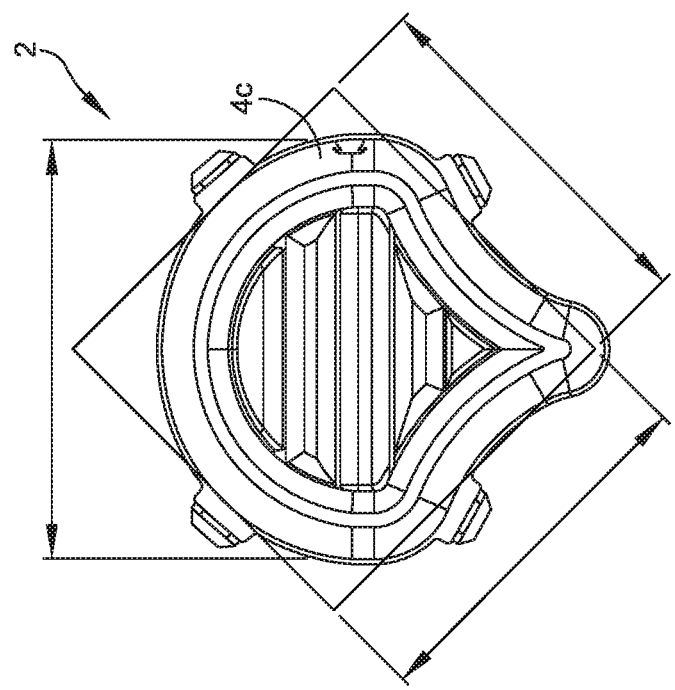
FIG. 1C illustrates a front view of the pneumatic chair jack of FIG. 1A, in accordance with some embodiments.

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship. In the claims, means-plus-function clauses, if used, are intended to cover structures described, suggested, or rendered obvious by the written description or drawings for performing the recited function, including not only structure equivalents but also equivalent structures.

In various embodiments, a multi-cell pneumatic chair jack is disclosed. The multi-cell pneumatic chair jack includes a plurality of single cell jack elements configured to transition a patient from a seated position to a standing position. Each of the single cell jack elements comprise a body defining a perimeter having a predetermined shape, such as a diamond shape, a saddle shape, a bike-seat shape, etc. The single cell jack elements are positioned under a patient in an uninflated state and inflated to raise the patient to a sitting position. In some embodiments, the single cell jack elements are configured for multistage inflation such that the perimeter of the single cell jack element inflates to stabilize a patient before the center of the single cell jack element inflates to raise the patient.

Figure 1B:
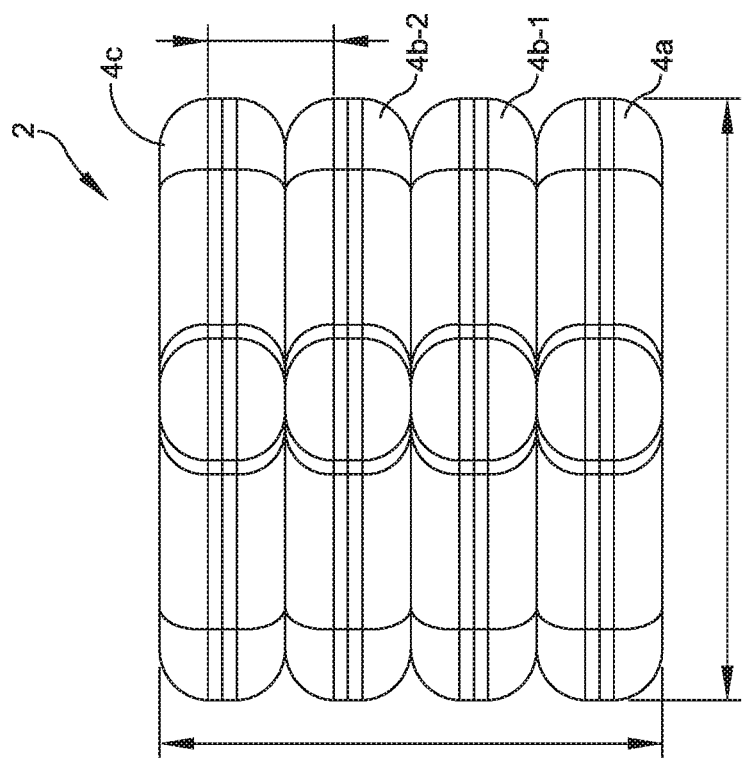
FIG. 1B illustrates top view of the pneumatic chair jack of FIG. 1A, in accordance with some embodiments.

FIG. 1A-1C illustrates one embodiment of a multi-cell pneumatic chair jack 2 including a plurality of single cell jack elements 4a, 4b_1, 4b_2, 4c (collectively "jack elements 4"). In the illustrated embodiment, each of the single cell jack elements 4 are attached (or coupled together) to form a multi-cell stack 5. The multi-cell pneumatic chair jack 2 can include any number of jack elements 4, such as, for example, one, two, three, four, and/or any number of jack elements 4. The number of jack elements 4 may be related to a height of a patient. In other embodiments, the multi-cell pneumatic chair jack 2 includes a predetermined number of jack elements 4 that are selectively inflated (or not inflated) based on a height of a user.

Figure 2:
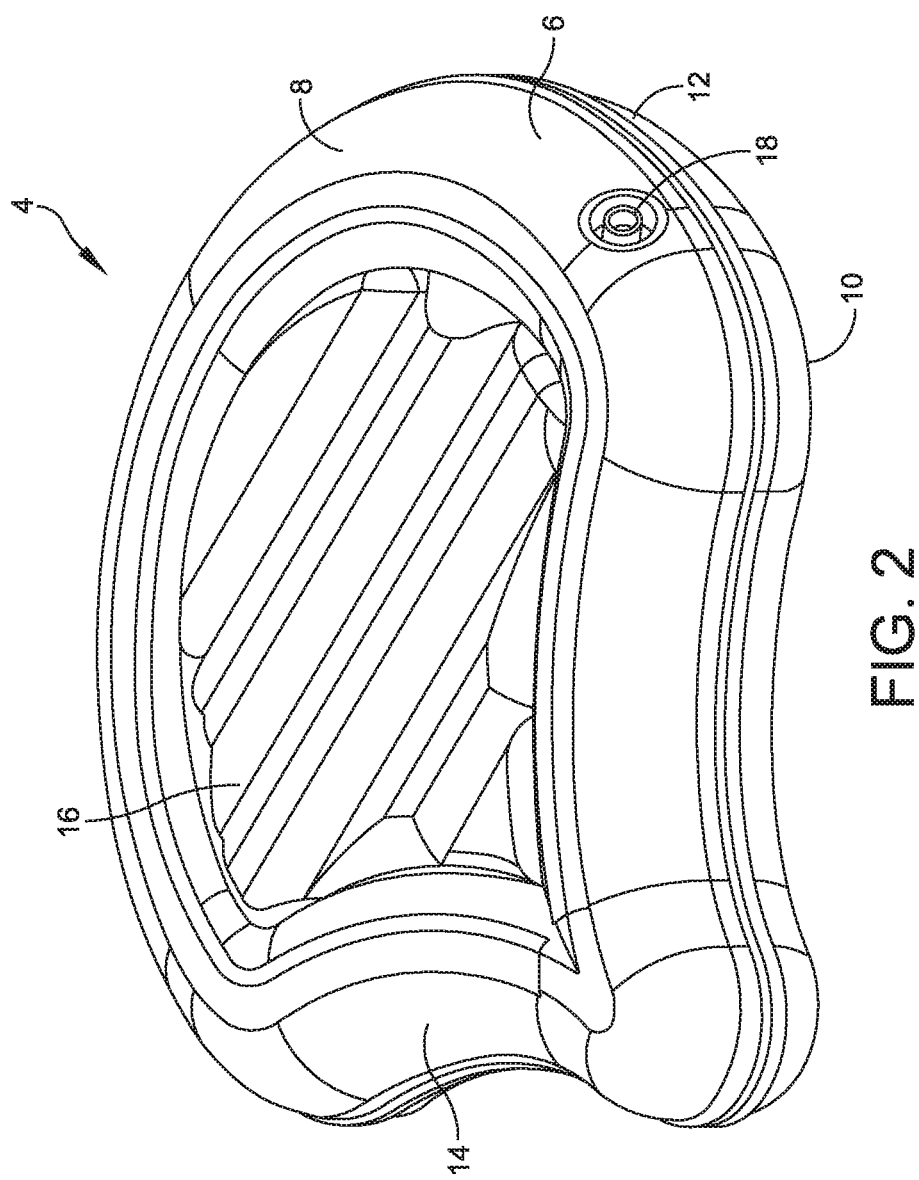
FIG. 2 illustrates a single cell jack element, in accordance with some embodiments.
Figure 8:
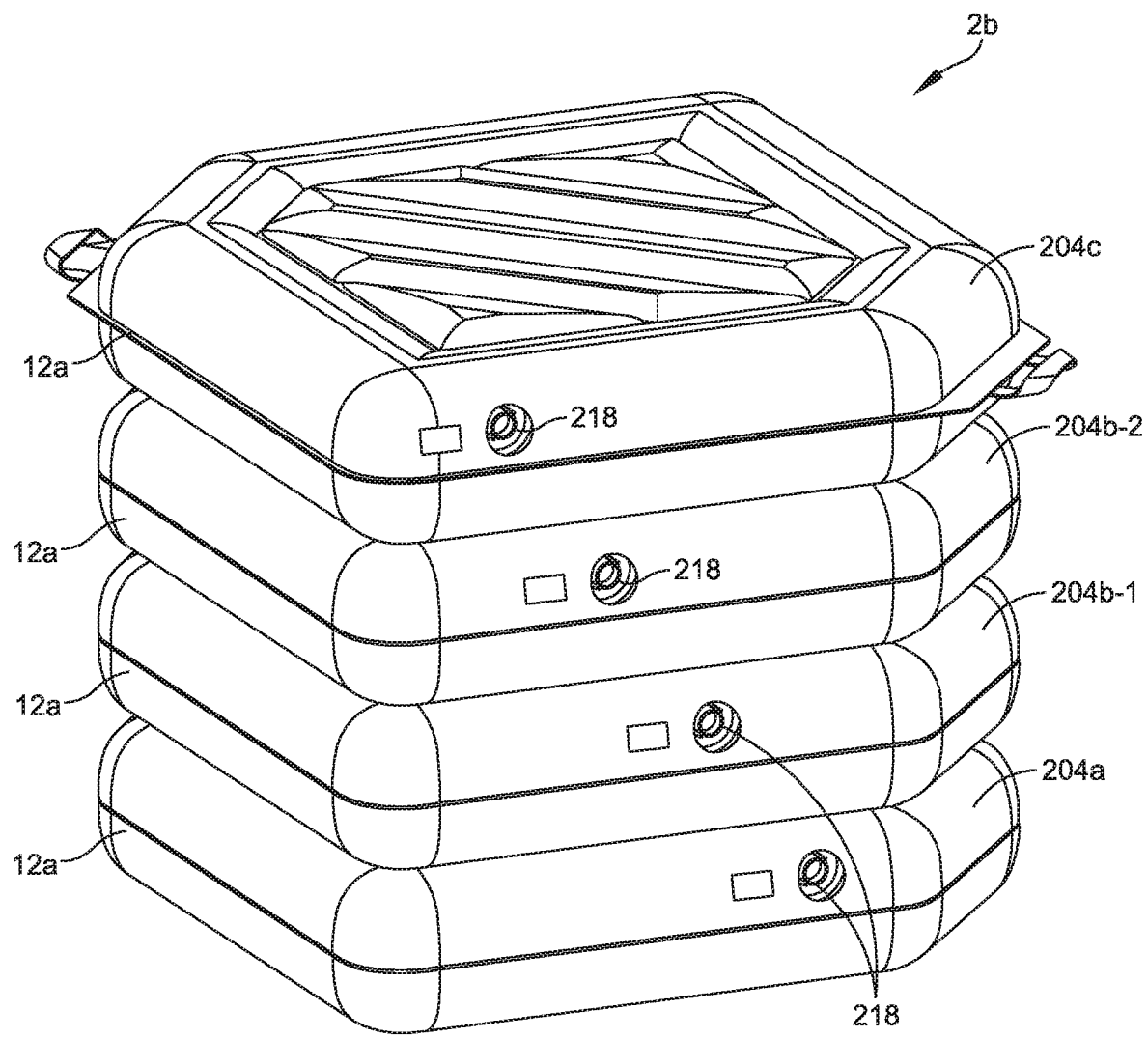
FIG. 8 illustrates a pneumatic chair jack including a plurality of single cell jack elements having a diamond shape, in accordance with some embodiments.

FIG. 2 illustrates one embodiment of a single cell jack element 4a. The single cell jack element 4a includes a body 6 defining an upper chamber portion 8 and a lower chamber portion 10. The upper and lower chamber portions 8, 10 are coupled together to define a perimeter 12. The perimeter 12 has a predetermined shape configured to position and stabilize a patient during a lifting procedure. In some embodiments, the perimeter 12 has a saddle and/or bike-seat shape (as illustrated in FIG. 2), a diamond shape (as illustrated in FIG. 8), and/or any other suitable shape. In some embodiments, the single cell jack element 4a is a lower (or first) jack element, although it will be appreciated that the jack element 4a can be configured as a middle (or second) and/or an upper (or third) jack element in various embodiments.

Figure 3:
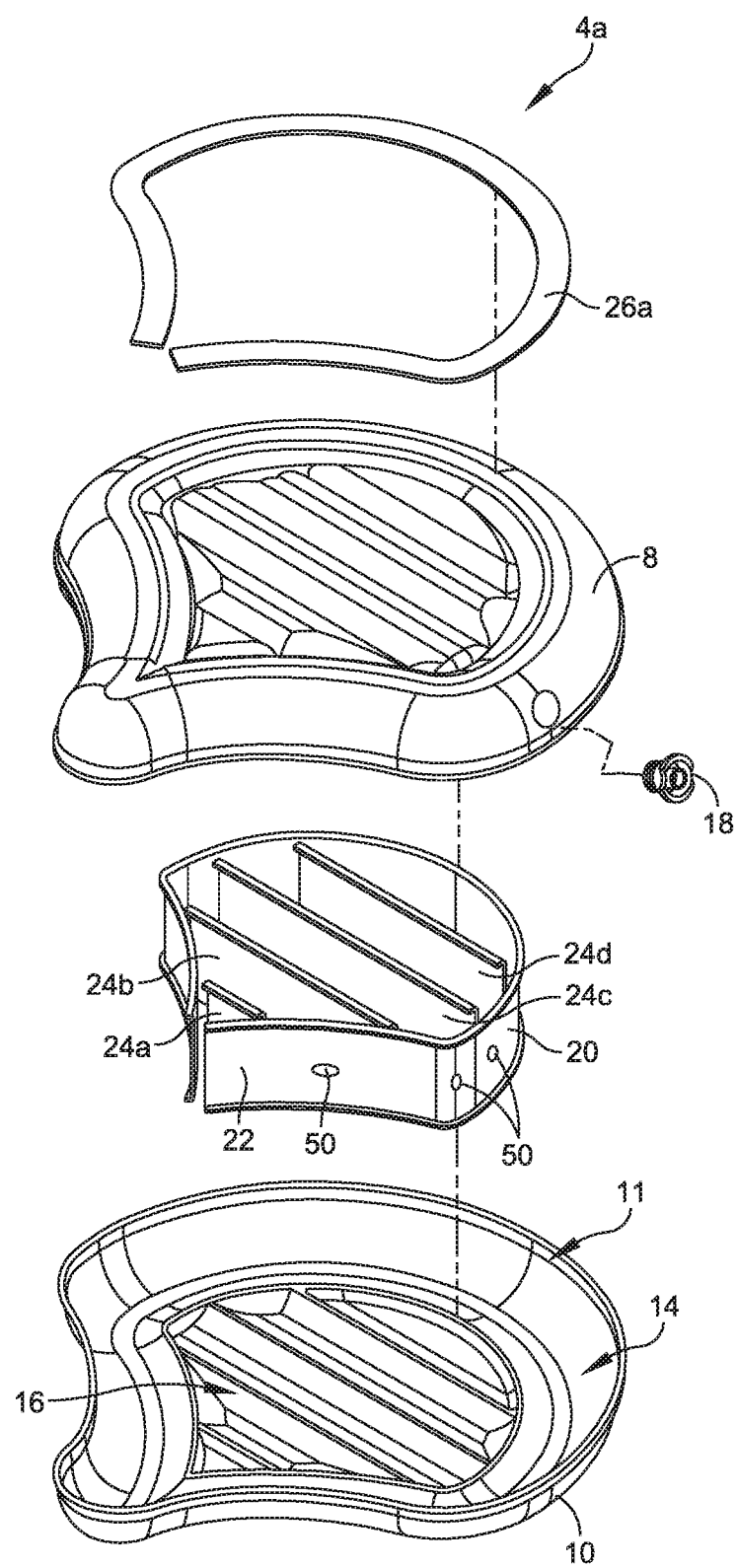
FIG. 3 illustrates an exploded view of a first single cell jack element, in accordance with some embodiments.

The upper chamber portion 8 and the lower chamber portion 10 are coupled together to define an inflation chamber 11 therebetween. As illustrated in FIG. 3 (and discussed in greater detail below), in some embodiments, the jack element 4a defines a perimeter chamber 14 and a central chamber 16. A valve 18 is coupled to at least one of the upper chamber portion 8 and/or the lower chamber portion 10. The valve 18 is configured to couple at least one of the perimeter chamber 14 and/or the central chamber 16 to an air source. Air is provided from the air source to inflate the perimeter chamber 14 and/or the central chamber 16. In some embodiments, the valve 18 is coupled to the perimeter chamber 14 and the central chamber 16 is coupled to the perimeter chamber 14. Air flows from the air source through the valve 18, into the perimeter chamber 14 and from the perimeter chamber 14 into the central chamber 16. In some embodiments, the perimeter chamber 14 is configured to substantially inflate prior to inflation of the central chamber 16. Although a single valve 18 is illustrated, it will be appreciated that the jack elements 4 can include one or more inflation valves, one or more deflation valves, and/or a combination of inflation valves, deflation valves, and/or two-way valves.

FIG. 3 illustrates an exploded view of a jack element 4a, in accordance with some embodiments. In some embodiments, the first jack element 4a includes flow control structure 20 located between the upper chamber portion 8 and the lower chamber portion 10. The flow control structure 20 includes a perimeter flow control stringer 22 and a plurality of lateral flow control stringers 24a-24b (collectively "flow control stringers 24"). In some embodiments, the perimeter flow control stringer 22 defines a vertical wall and/or separation between a perimeter chamber 14 and a central chamber 16. The perimeter flow control stringer 22 can define a perimeter shape matching the perimeter 12 of the jack element 4a and/or can define a shape other than the perimeter 12. In some embodiments, the perimeter flow control stringer 22 defines one or more openings 50 therethrough. The openings 50 are sized and configured to provide a predetermined rate of air flow from the perimeter chamber 14 to the central chamber 16. In some embodiments, the openings 50 include one or more lengthwise slits and/or round holes in the perimeter flow control stringer 22. For example, in some embodiments, the openings 50 include one or more lengthwise slits having a predetermined length, such as a length between about ¼" to about 1", ¼" to about ⅝", and/or any other suitable range. As another example, in some embodiments, one or more openings 50 include one or more holes having a predetermined diameter, such as a diameter between about 0.1"-0.5", 0.1"-0.3", and/or any other suitable diameter. It will be appreciated that the sizes of the openings 50 presented herein are exemplary and that the openings 50 can be configured with any size to provide any predetermined inflation rate of the central chamber 16.

In some embodiments, a plurality of lateral flow control stringers 24 are positioned within the central chamber 16. The lateral flow control stringers 24 are configured to control inflation of the central chamber 16. The lateral flow control stringers 24 can include one or more openings (not shown). In some embodiments, the perimeter flow control stringer 22 and/or the lateral flow control stringers 24 are configured such that the perimeter chamber 14 inflates prior to inflation of the central chamber 16. Inflation of the perimeter chamber 14 provides stability to and proper positioning of a patient on a jack element 4a prior to inflation of the central chamber 16 to lift the patient. The perimeter flow control stringer 22 and/or the lateral flow control stringers 24 can be selected to provide any desirable ratio between inflation of the perimeter chamber 14 and the central chamber 16.

In some embodiments, the perimeter flow control stringer 22 and/or the flow control stringers 24 are sized and configured to control inflation of the central chamber 16. For example, in some embodiments, the openings 50 in the perimeter flow control stringer 22 and/or the flow control stringers 24 are configured to provide inflation of the central chamber 16 from front to back, e.g., a proximal portion 16a of the central chamber 16 inflates prior to a distal portion 16 of the central chamber 16. Front-to-back inflation causes a patient to shift towards the distal end 16b of the chamber 16 and provides additional stability. As another example, in some embodiments, the openings 50 and/or the lateral flow control stringers 24 are configured to provide inflation of the central chamber 16 from back to front, e.g., a distal portion of the central chamber 16 inflates prior to a proximal portion 16a of the central chamber 16. Back-to-front inflation causes a patient to shift towards the proximal end 16a of the central chamber 16.

In some embodiments, a fastener 26a is coupled to at least one of the upper chamber portion 8 and/or the lower chamber portion 10. The fastener 26a is configured to couple the jack element 4a to one or more additional jack elements 4. In the embodiment illustrated in FIG. 3, the fastener 26a is located on an upper surface of the upper chamber portion 8, although it will be appreciated that the fastener 26a can be positioned on any suitable portion of the jack element 4a, such as any portion of the upper chamber portion 8, lower chamber portion 10, and/or a combination thereof. The fastener 26a can comprise any suitable fastening mechanism, such as, for example, a removable, non-removable, and/or permanent fastener. Example fastening mechanisms include, but are not limited to, radiofrequency (RF) welding, adhesives, hook-and-loop, weldable hook fasteners, and/or any other suitable fastening mechanism. The fastener 26a can extend over the entirety of and/or a portion of the upper chamber portion 8 and/or the lower chamber portion 10.

Figure 4:
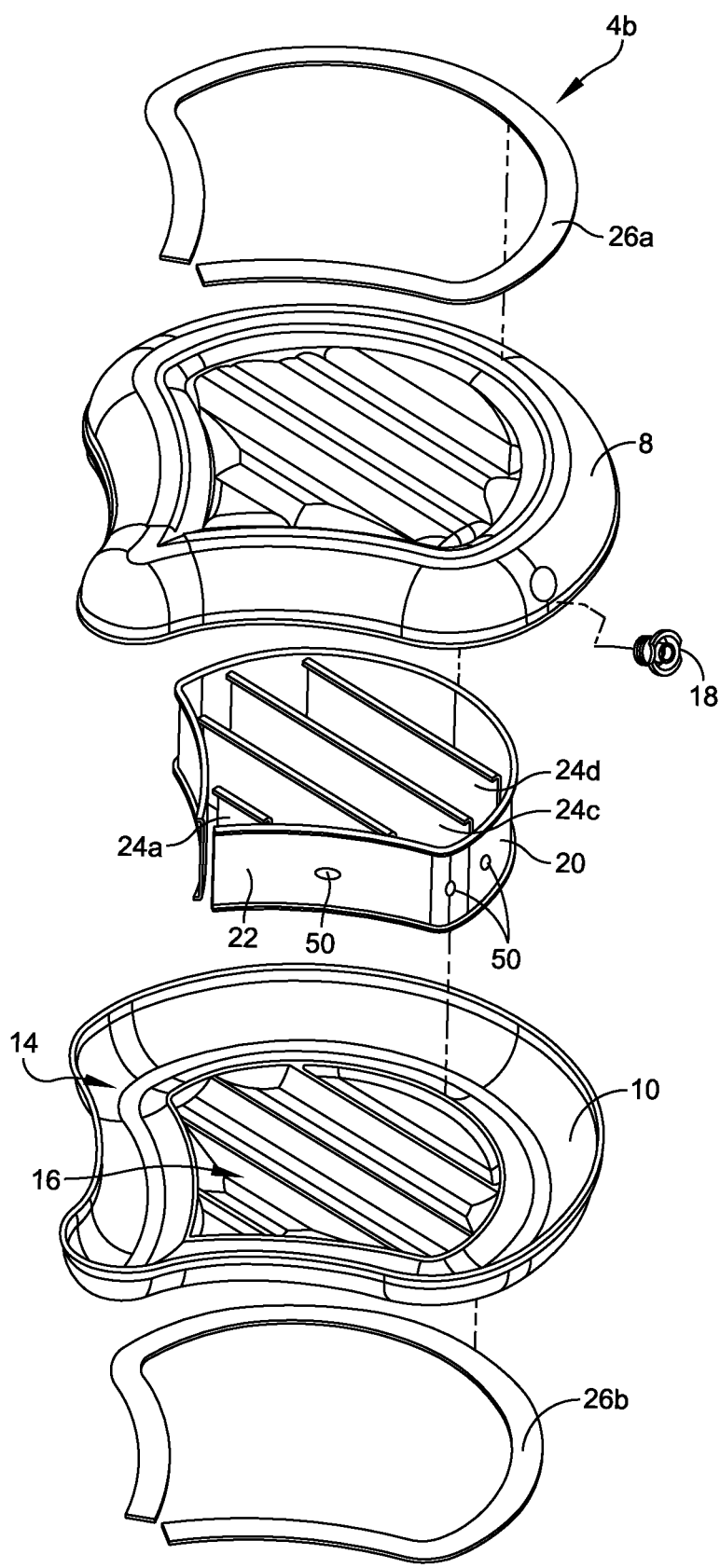
FIG. 4 illustrates an exploded view of a second single cell jack element, in accordance with some embodiments.

FIG. 4 illustrates one embodiment of a middle (or second) jack element 4b including a first fastener 26a coupled to an upper chamber portion 8 and a second fastener 26b coupled to a lower chamber portion 10. The middle jack element 4b is similar to the lower jack element 4a described above, and similar description is not repeated herein. The middle jack element 4b is configured to be located between a lower jack element 4a and one or more additional jack elements 4b-4c. The first and second fasteners 26a, 26b are configured to permanently and/or removably couple the middle jack element 4b to one or more additional jack elements 4b-4c. In some embodiments, the middle jack element 4b can have a different inflation profile than the lower jack element 4a, for example, inflating at a faster/slower rate and/or at a different inflation ratio between perimeter chamber 14 and a central chamber 16.

Figure 5:
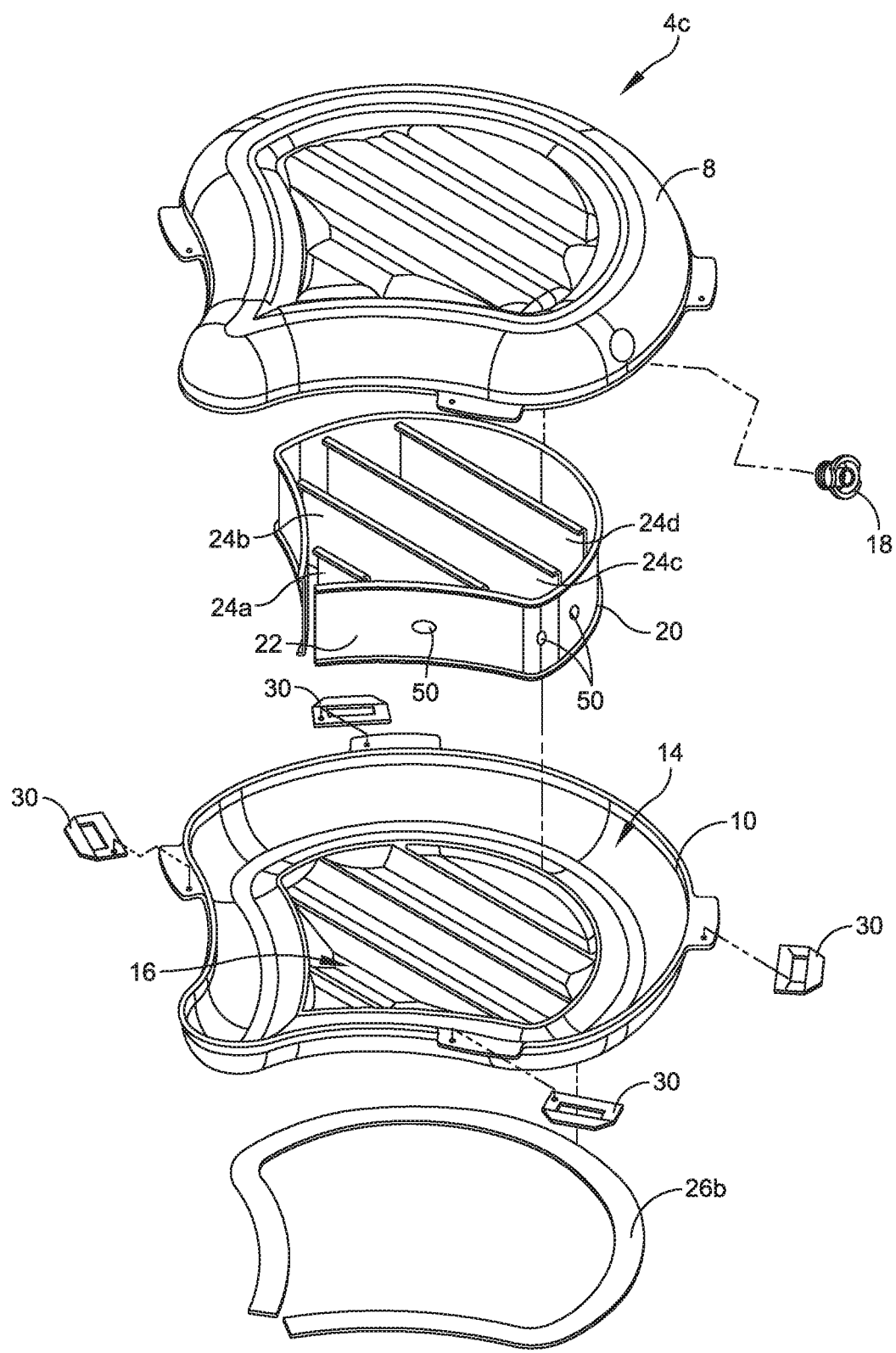
FIG. 5 illustrates an exploded view of a third single cell jack element, in accordance with some embodiments.

FIG. 5 illustrates one embodiment of a lower jack element 4c including a fastener 26b formed on a lower chamber portion 10. The third jack element 4c is similar to the first jack element 4a described above, and similar description is not repeated herein. The third jack element 4c includes a fastener 26b only on the lower chamber portion 10 and is configured to be positioned at the top of a stack jack elements 4 defining a multi-cell pneumatic jack 2. The fastener 26b is configured to couple the third jack element 4c to at least one of a first jack element 4a and/or a second jack element 4b.

In some embodiments, one or more of the jack elements 4 includes at least one handle 30. For example, as shown in FIG. 5, in some embodiments, the third jack element 4c includes at least one handle 30 coupled to a perimeter 12 thereof. The handles 30 are sized and configured to allow a user, such as patient, first-responder, nurse, and/or other user, to grip the handle 30. In some embodiments, the handles 30 are positioned to allow a patient and/or a caregiver to grip the handles 30 during inflation to provide additional stability to and/or assist in positioning of a patient. For example, in some embodiments, one or more jack elements 4, such as an upper jack element 4c, include four handles 30 distributed about the periphery of the jack element 4, two at the front and two at the rear. The front handles 30 are configured to allow a patient to grip the handles 30 and stabilize themselves (e.g., balance) during inflation. The rear handles 30 can be configured for a caregiver or other user to provide stability to the jack elements 4 during inflation. The illustrated embodiment includes four handles 30, although it will be appreciated that a jack element 4 can include one, two, three, four, and/or any other suitable number of handles.

Referring back to FIG. 1, in some embodiments, the multi-cell pneumatic jack 2 includes a plurality of jack elements 4 arranged in an aligned multi-cell stack 5. The plurality of jack elements 4 includes a first jack element 4a positioned at the bottom of the stack 5. The first jack element 4a includes a fastener 26a formed on an upper chamber surface 8. In some embodiments, the lower chamber surface 10 can comprise a non-slip surface and/or non-slip coating to prevent movement of the multi-cell pneumatic jack 2 during inflation. One or more middle jack elements 4b_1, 4b_2 (collectively "middle jack elements 4b") are positioned above the lower jack element 4a. The middle jack elements 4b include a first fastener 26a on an upper chamber surface 8 and a second fastener 26b on the lower chamber surface 10. The first fastener 26a couples a first middle jack element 4b_1 to the lower jack element 4a. The first middle jack element 4b_1 is attached to a second middle jack element 4b_2, for example, by a first fastener 26a formed on the first middle jack element 4b_1 and a second fasteners 26b formed on the second middle jack element 4b_2. In some embodiments, an upper jack element 4c is positioned above the lower and middle jack elements 4a, 4b. The upper jack element 4c includes a fastener 26b only on a lower chamber surface 10. Although the illustrated embodiments include jack elements 4 having similar heights, it will be appreciated that the jack elements 4 can have different dimensions than other jack elements 4, including having one or more heights, widths, and/or lengths.

In some embodiments, the perimeter chamber 14 and/or the central chamber 16 of a first of the plurality of jack elements 4 can be coupled to the perimeter chamber 14 and/or the central chamber 16 of a second of the plurality of jack elements 4. For example, in some embodiments, a lower jack element 4a includes a perimeter chamber 14 and a central chamber 16. The lower jack element 4a can be permanently attached to a middle jack element 4b_1. The perimeter chamber 14 of the lower jack element 4a and the middle jack element 4b 1 can each include an opening configured to couple the perimeter chamber 14 of the lower jack element 4a to the perimeter chamber 14 of the middle jack element 4b_1). In some embodiments, the middle jack element 4b_1 can be attached to additional jack elements 4b_2, 4c to allow air flow from the perimeter chamber 14 and/or the central chamber of the middle jack element 4b_1 into the perimeter chamber 14 and/or the central chamber 16 of one or more additional jack elements 4b 2, 4c.

Figure 9:
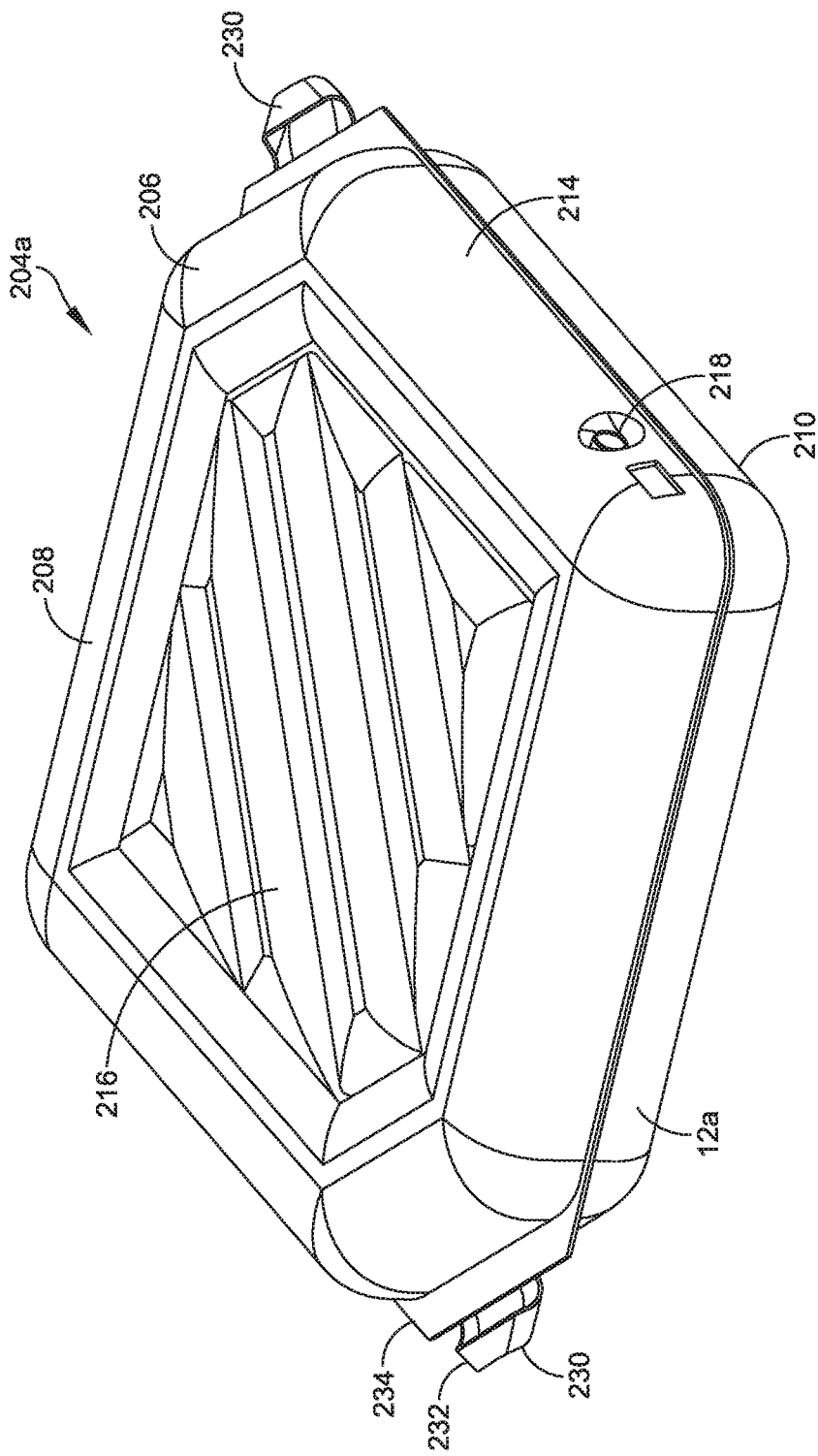
FIG. 9 illustrates a single cell jack element of the pneumatic chair jack of FIG. 8, in accordance with some embodiments.
Figure 10:
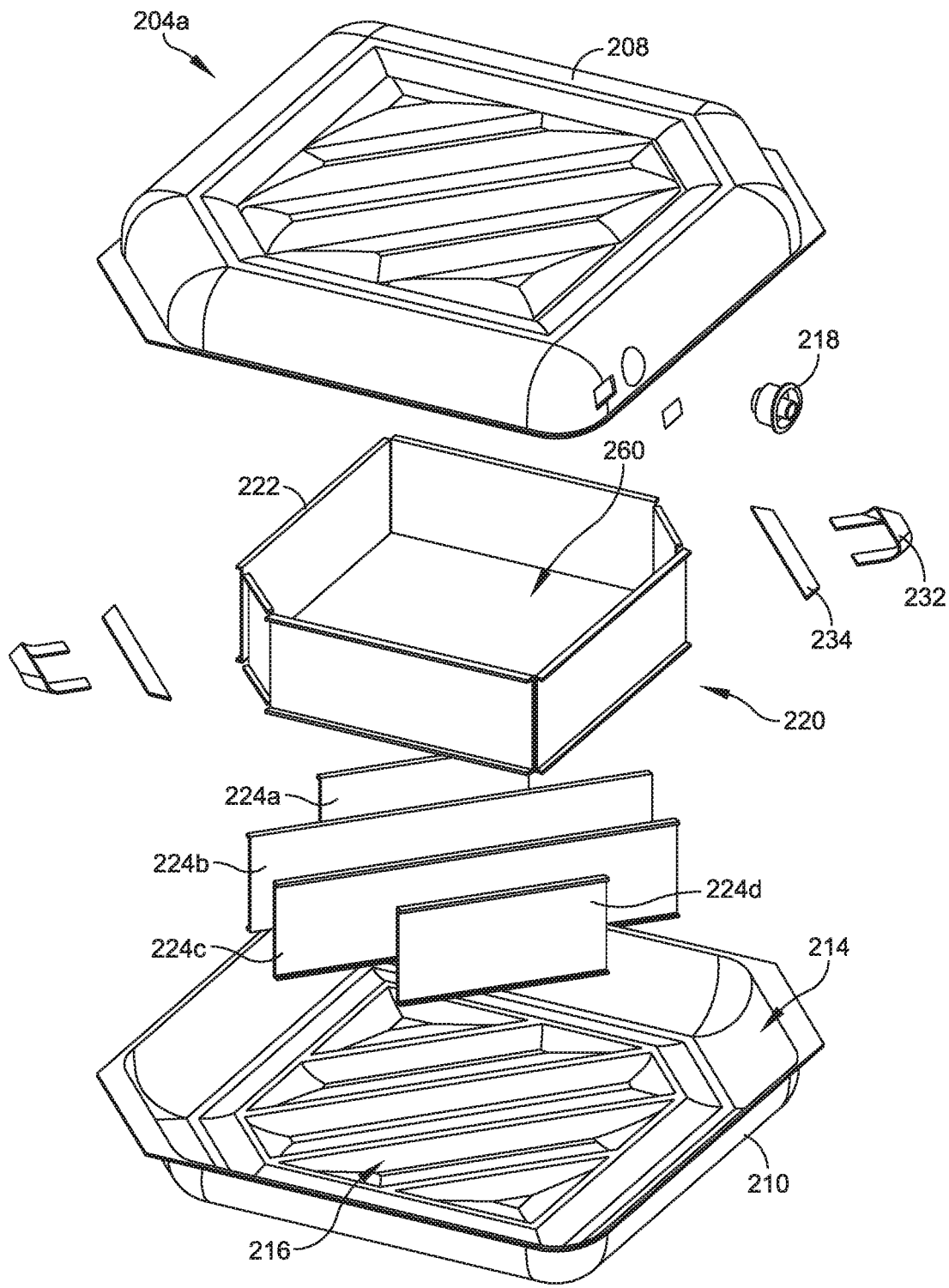
FIG. 10 illustrates an exploded view of the single cell jack element of FIG. 9, in accordance with some embodiments.

FIGS. 8-10 illustrate an embodiment of a multi-cell pneumatic jack 2b including a plurality of jack elements 204a. 204b_1, 204b_2, 204c (collectively "jack elements 204"), in accordance with some embodiments. The multi-cell pneumatic jack 2b is similar to the multi-cell pneumatic jack 2 described above in conjunction with FIGS. 1-5, and similar description is not repeated herein. Each of the jack elements 204 includes a diamond-shaped perimeter 12a, although it will be appreciated that one or more of the jack elements 204 can include an alternative and/or additional shape to those discussed herein. In some embodiments, a position of a valve 218 on each of the plurality of jack elements 204 is selected to provide a staggered and/or offset position for each valve 218 with respect to a valve 218 of a jack element 204 positioned above and/or below a respective jack element 204. For example, in the illustrated embodiments, each of the jack elements 204 includes a valve 218 that is offset with respect to a jack element 204 positioned above and/or below to provide a staggered (or diagonal stack) of valves 218.

FIG. 10 illustrates an exploded view of a selected one 204a of the plurality of jack elements 204a-204c. The jack element 204a includes an upper chamber portion 208 and a lower chamber portion 210 defining an inflation chamber 211. A flow control structure 220 divides the inflation chamber 211 into a perimeter chamber 214 and a central chamber 216. The flow control structure 220 is configured to control inflation of the jack element 204a when an inflation device is coupled to the valve 218. In some embodiments, the flow control structure 220 includes a perimeter stringer 222 and a plurality of lateral flow control stringers 224a-224d (collectively "lateral flow control stringers 224"). The plurality of lateral flow control stringers 224 are positioned within an internal volume 260 defined by the perimeter stringer 222. The perimeter stringer 222 and the later flow control stringers 224 direct air flow within the internal chamber 211 of the jack element 204a. For example, in some embodiments, the perimeter stringer 222 and/or the lateral flow control stringers 224 are configured such that a perimeter chamber 214 of the jack element 204a is substantially inflated prior to inflation of a central chamber 216, as described above in conjunction with jack element 4a.

In some embodiments, the jack element 204a includes a two-way valve 218 configured to selectively provide inflation and/or deflation of the jack element 204a. For example, in various embodiments, the two-way valve 218 can be positioned at a plurality of positions corresponding to inflation, partial deflation, and/or total deflation of the jack element 204a. An air supply hose can be coupled to the two-way valve 218 to provide air flow to and/or from the internal chamber 211 of the jack element 204a. Two-way flow control valves are described in greater detail in International Patent Appl. Serial No. PCT/US18/25309, which is incorporated herein by reference in its entirety.

In some embodiments, the jack element 204a includes at least one handle 230 coupled to the body 206. The handle 230 can include a gripping portion 232 and an attachment portion 234. The gripping portion 232 is coupled to the attachment portion 234 and the attachment portion 234 is coupled to the upper chamber portion 208 and/or the lower chamber portion 210. Although embodiments are illustrated with two handles 230, it will be appreciated that the jack element 204 can include any number of handles 230, such as, for example, zero, one, two, four, etc.

Figure 6:
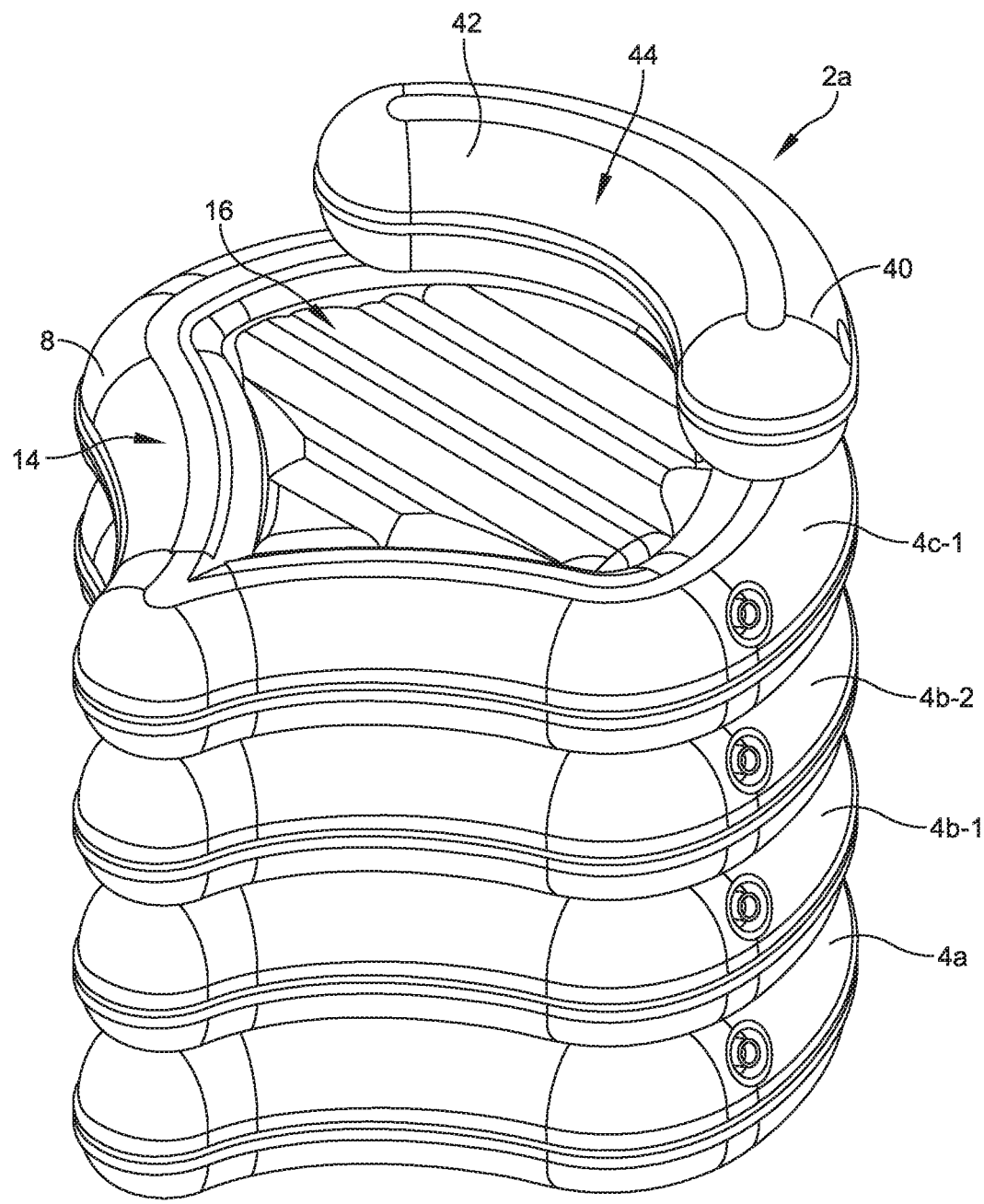
FIG. 6 illustrates a pneumatic chair jack including at least one jack element having an inflatable back rest, in accordance with some embodiments.
Figure 7:
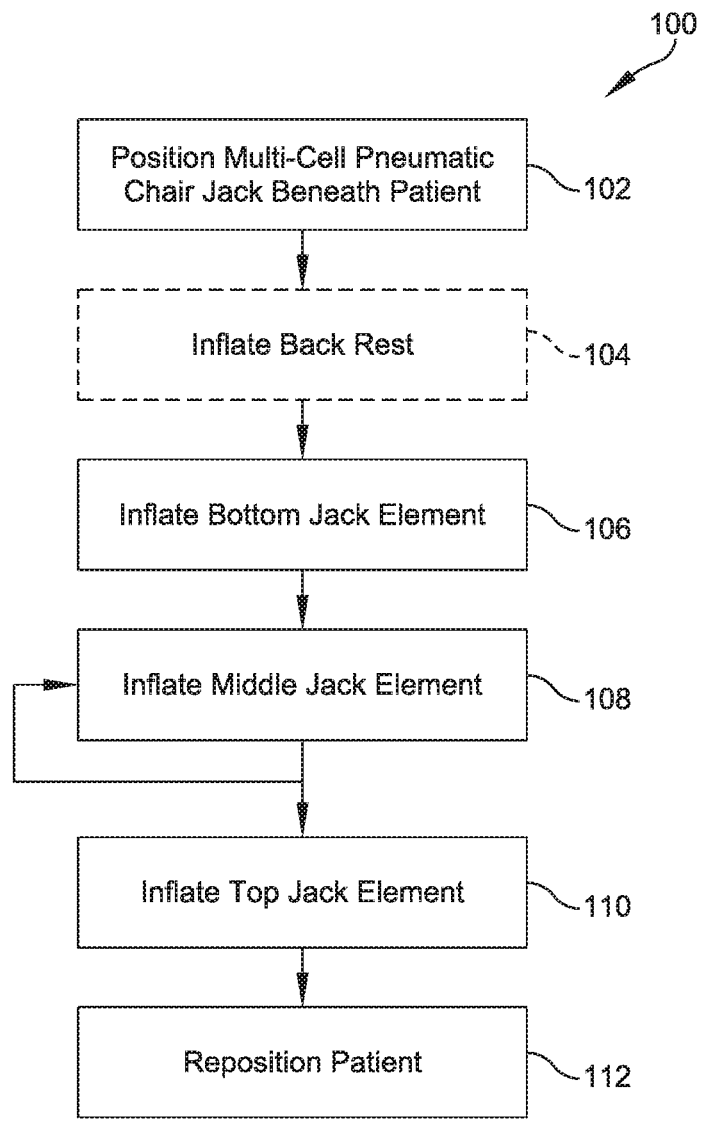
FIG. 7 illustrates a method of raising a patient from a seated position to a standing position, in accordance with some embodiments.

FIG. 6 illustrates one embodiment of a multi-cell pneumatic jack 2a including at least one jack element 4c_1 having an inflatable back rest 40. The multi-cell pneumatic jack 2a includes at least one lower jack element 4a and one or more middle jack elements 4b (e.g., two middle jack elements 4b_1, 4b_2) similar to the multi-cell pneumatic jack 2 discussed above, and similar description is not repeated herein. An upper jack element 4c_1 includes an inflatable back rest 40 attached to the upper chamber portion 8. The inflatable back rest 40 includes an side wall 42 defining an inner chamber 44. The inner chamber 44 is in fluid communication with one of the perimeter chamber 14 and/or the central chamber 16 of the upper jack element 4c_1. When the upper jack element 4c_1 is inflated, via the valve 18, air flows from the perimeter chamber 14 and/or the central chamber 16 into the inner chamber 44 of the inflatable back rest 40. The inflatable back rest 40 is sized and configured to position a patient and/or maintain a position of a patient with respect to the upper jack element 4c_1.

In some embodiments, the inflatable back rest 40 is a separate element from the upper jack element 4c_1. The inflatable back rest 40 can include a valve 18 coupled to a side wall 42 thereof. The inflatable back rest 40 may be independently inflated before, during, and/or after inflation of one or more of the jack elements 4 of the multi-cell pneumatic jack 2. The inflatable back rest 40 can include a fastener (not shown) configured to permanently and/or releasably couple the inflatable back rest 40 to the upper jack element 4c.

With reference now to FIGS. 1-7, a method 100 of using the multi-cell pneumatic jack 2 is disclosed. The multi-cell pneumatic jack 2 can be configured to lift a user and/or patient from a sitting position, such as on a floor/ground, chair, and/or other surface, to a standing position. At step 102, a multi-cell pneumatic jack 2 including a plurality of jack elements 4 is positioned beneath a user in a seated position. The multi-cell pneumatic jack 2 can include any number of individual single cell jack elements 4, such as, for example, four jack elements 4. The jack elements 4 can be permanently and/or releasably attached together.

At optional step 104, an inflatable back rest 40 attached to one or more of the jack elements 4 is inflated. For example, in some embodiments, an inflatable back rest 40 is permanently and/or releasably attached to an upper jack element 4c prior to insertion of the multi-cell pneumatic jack 2 beneath the patient. The inflatable back rest 40 can be inflated simultaneously with and/or prior to inflation of a jack element, such as an upper jack element 4c.

At step 106, a selected first of the plurality of jack elements 4 of the multi-cell jack 2 is inflated by coupling the selected first of the plurality of jack elements 4 to an inflation device (not shown). For example, an inflation hose (or other device) may be coupled to a valve 18 formed integrally with the selected first of the plurality of jack elements 4. For example, in some embodiments, the selected first of the plurality of jack elements 4 is an upper jack element 4c positioned at an upper-most position on a multi-cell stack 5. Inflation of the upper jack element 4c may advantageously position a patient centrally on the multi-cell jack 2 and/or provide simultaneous inflation of a back rest 40 to position a patient. As another example, in some embodiments, the selected first of the plurality of jack elements 4 is a lower jack element 4a positioned at a lower-most position on a multi-cell stack 5. Inflation of the lower jack element 4a may advantageously provide maximum contact between a non-slip surface defined by the lower jack element 4a and a surface positioned beneath the multi-cell jack 2. Although specific embodiments are discussed herein, it will be appreciated that any of the jack elements 4 may be selected for inflation during step 106. A perimeter chamber 14 and the central chamber 16 of the selected first of the plurality of jack elements 4 each inflate at a predetermined rate. In some embodiments, the perimeter chamber 14 is configured to substantially inflate prior to inflation of the central chamber 16. Inflation of the perimeter chamber 14 positions the patient in a predetermined position on the multi-cell jack 2, for example, centered on one or more of the single cell jack elements 4. The selected first of the plurality of jack elements 4 is inflated and raises the user a first predetermined height.

At step 108, a selected second of the plurality of jack elements 4 is inflated. The selected second of the plurality of jack elements 4 may include a lower jack element 4b, a middle jack element 4b_1, 4b_2 positioned between additional jack elements 4 in the multi-cell stack 5, or an upper jack element 4c. The selected second of the plurality of jack elements 4 further raises the patient to a second predetermined height. The width of each of the jack element 4 can be greater than, lesser than, or equal to the height of the selected first of the plurality of jack elements 4. In some embodiments, step 108 is repeated for one or more additional jack elements 4 (such as one or more additional middle jack elements 4b_2) to increase a height of the patient. For example, in some embodiments, a predetermined number of middle jack elements 4b can be included in a multi-cell jack 2. A user (such as a caregiver) can selectively inflate some or all of the middle jack elements 4b to raise a patient to a predetermined height to facilitate transition of the patient from a sitting position to a standing position. It will be appreciated that the number of middle jack elements 4b inflated can vary based on the height of a patient and the ability of a patient to transition to a full standing position from a partial seated position.

At step 110, a selected third of the plurality of jack elements 4 is inflated to raise the user to a final height such that a user can stand while exerting minimum effort. For example, in some embodiments, the selected third of the plurality of jack elements 4 can include an upper jack element 4a, a middle jack element 4b_1, 4b_2, or a lower jack element 4c. In some embodiments, inflation of one or more of the jack elements 4 is omitted if the patient reaches a sufficient height for standing prior to inflation of all of the jack elements 4. At an optional step 112, the patient can be repositioned after inflating one or more of the jack elements 4 and prior to standing up from the multi-cell jack 2.

Although the subject matter has been described in terms of exemplary embodiments, it is not limited thereto. Rather, the appended claims should be construed broadly, to include other variants and embodiments, which may be made by those skilled in the art.

What is claimed is:

1. A jack element, comprising
a body having a predetermined perimeter shape and defining a perimeter chamber and a central chamber;
a valve coupled to the body and configured to provide air flow to the perimeter chamber, and wherein the perimeter chamber is coupled to the central chamber;
a plurality of flow control stringers located between the perimeter chamber and the central chamber, wherein the plurality of flow controlled stringers are configured to control an air flow rate into each of the perimeter chamber and the central chamber, wherein the plurality of flow control stringers comprise a perimeter stringer and a plurality of lateral flow control stringers positioned within an internal volume defined by the perimeter stringer, wherein the perimeter chamber is configured to substantially inflate prior to inflation of the central chamber when air flow from an air source is provided through the valve, and wherein the plurality of lateral flow control stringers are configured to provide inflation of a first portion of the central chamber prior to inflation of a second portion of the central chamber, and wherein each of the plurality of flow control stringers define at least one lengthwise slit; and
at least one fastener formed on the body and configured to attach the jack element to at least one additional jack element in a multi-cell stack, and wherein the at least one additional jack element includes a body having a similar predetermined perimeter shape as the predetermined perimeter shape defined by the body.

2. The jack element of claim 1, comprising at least one handle coupled to the body.

3. The jack element of claim 1, wherein the perimeter stringer defines a shape substantially similar to the perimeter shape of the body, wherein the perimeter chamber is defined between the perimeter stringer and the body and the central chamber is defined by the internal volume defined by the perimeter stringer.

4. The jack element of claim 1, wherein the predetermined perimeter shape of the body is selected from the group consisting of a diamond shape, a saddle shape, and a seat shape.

5. The jack element of claim 1, wherein the at least one fastener comprises a first fastener positioned on an upper surface of the body and a second fastener positioned on a lower surface of the body.

6. The jack element of claim 1, wherein the at least one fastener is a releasable fastener.

7. A system, comprising:
a first jack element; and
a second jack element, wherein each of the first and second jack elements comprise:
a body having a predetermined perimeter shape and defining a perimeter chamber and a central chamber;
a valve coupled to the body and configured to provide air flow to the perimeter chamber;
a plurality of flow control stringers located between the perimeter chamber portion and the central chamber portion, wherein the plurality of flow control stringers are configured to control an air flow rate into each of the perimeter chamber and the central chamber, wherein the plurality of flow control stringers comprise a perimeter stringer and a plurality of lateral flow control stringers positioned within an internal volume defined by the perimeter stringer, wherein the lateral flow control stringers are configured to provide inflation of a first portion of the central chamber prior to inflation of a second portion of the central chamber when air flow from an air source is provided through the valve, and wherein each of the plurality of flow control stringers define at least one lengthwise slit; and
at least one fastener formed on the body,
wherein the first jack element is coupled to the second jack element by the at least one fastener on each of the first jack element and the second jack element.

8. The system of claim 7, comprising a third jack element, wherein the third jack element is configured to be located between the first jack element and the second jack element, and wherein a perimeter chamber or a central chamber of the third jack element is coupled to an associated one of the perimeter chamber or the central chamber in each of the first jack element and the second jack element.

9. The system of claim 7, comprising an inflatable back rest configured to be attached to one of the first jack element or the second jack element.

10. The system of claim 7, wherein the perimeter stringer defines a shape substantially similar to the perimeter shape of the body, wherein the perimeter chamber is defined between the perimeter stringer and the body and the central chamber is defined by the internal volume defined by the perimeter stringer.

11. The system of claim 10, wherein the perimeter stringer defines a plurality of openings therethrough, and wherein the openings are sized and configured to provide a predetermined rate of air flow from the perimeter chamber to the central chamber.

12. The system of claim 7, wherein the predetermined perimeter shape of each of the bodies is selected from the group consisting of a diamond shape, a saddle shape, and a seat shape.

13. The system of claim 7, wherein the first jack element is releasably attached to the second jack element by the at least one fastener.

14. The system of claim 7, wherein the first jack element is fixedly attached to the second jack element by the at least one fastener.

15. A method of raising a patient, comprising:
- positioning a multi-cell inflatable jack under a patient, wherein the multi-cell inflatable jack comprises a plurality of inflatable jack elements, wherein each of the plurality of inflatable jack elements comprises:
  - a body having a predetermined perimeter shape and defining a perimeter chamber and a central chamber;
  - a valve coupled to the body and configured to provide air flow to the perimeter chamber;
  - a plurality of flow control stringers located between the perimeter chamber portion and the central chamber portion, wherein the plurality of flow control stringers are configured to control an air flow rate into each of the perimeter chamber and the central chamber, wherein the plurality of flow control stringers comprise a perimeter stringer and a plurality of lateral flow control stringers positioned within an internal volume defined by the perimeter stringer, wherein the lateral flow control stringers are configured to provide inflation of a first portion of the central chamber prior to inflation of a second portion of the central chamber when air flow from an air source is provided through the valve, and wherein each of the plurality of flow control stringers define at least one lengthwise slit; and
  - at least one fastener formed on the body, wherein the first jack element is configured to be coupled to the second jack element by the at least one fastener on each of the first jack element and the second jack element;
- inflating a first of the plurality of inflatable jack elements to raise a patient from a seated position to a first height; and
- inflating a second of the plurality of inflatable jack elements to raise a patient from the first height to a second height, wherein the second height is configured to position the patient in a standing position.

16. The method of claim 15, comprising inflating an inflatable back rest attached to the first of the plurality of inflatable jack elements prior to inflation of the first of the plurality of inflatable jack elements.

\* \* \* \* \*